United States Patent [19]

Rennie

[11] Patent Number: 5,368,843
[45] Date of Patent: Nov. 29, 1994

[54] THICKENING SYSTEM

[75] Inventor: George K. Rennie, Bebington, Great Britain

[73] Assignee: Lever Brothers Company, Division of Conopco, Inc., New York, N.Y.

[21] Appl. No.: 72,683

[22] Filed: Jun. 4, 1993

Related U.S. Application Data

[63] Continuation of Ser. No. 713,050, Jun. 10, 1991, abandoned, which is a continuation of Ser. No. 361,514, Jun. 5, 1989, abandoned.

[30] Foreign Application Priority Data

Jun. 8, 1988 [GB] United Kingdom ................ 8813552

[51] Int. Cl.$^5$ ..................... A61K 7/16; C11D 3/37; C11D 3/22; C11D 17/00
[52] U.S. Cl. ................... 424/49; 252/313.1; 252/174.23
[58] Field of Search ............... 252/313.1, 313.2, 315.3, 252/315.4, 174.23, 174.24, 174.25; 424/49, 58

[56] References Cited

U.S. PATENT DOCUMENTS

| | | | |
|---|---|---|---|
| 3,658,734 | 4/1972 | Pettitt | 524/55 |
| 4,299,710 | 11/1981 | Dupre et al. | 252/114 |
| 4,347,153 | 8/1982 | Hooper et al. | 252/174.25 |
| 4,540,510 | 9/1985 | Karl | 252/315.3 |
| 4,610,870 | 9/1986 | Jain et al. | 424/19 |
| 4,687,663 | 8/1987 | Schaeffer | 514/944 X |
| 4,786,198 | 11/1988 | Zgambo | 106/23 X |
| 4,787,998 | 11/1988 | Rennie et al. | 252/174.11 |
| 4,798,682 | 1/1989 | Ansmann | 252/312 |
| 4,828,833 | 5/1989 | Cordon | 424/49 X |
| 4,840,811 | 6/1989 | Bayerlein et al. | 426/430 OR |
| 5,057,241 | 10/1991 | Merritt et al. | 252/DIG. 2 |
| 5,286,405 | 2/1994 | Rennie et al. | 252/174.23 X |

FOREIGN PATENT DOCUMENTS

| | | | |
|---|---|---|---|
| 152095 | 8/1985 | European Pat. Off. | |
| 0174689 | 3/1986 | European Pat. Off. | 252/356 |
| 1549378 | 8/1979 | United Kingdom | |
| 2026341 | 2/1980 | United Kingdom | 252/313.1 |

OTHER PUBLICATIONS

Roy L. Whistler, Industrial Gums Polysaccharides and Their Derivatives, 2nd Ed. (Academic Press, New York, 1973) p. 493.
European Search Report & Annex.
Technical Bulletin DB-15 (Kelzan xanthum gum).
Technical Bulletin for Shellflo biopolymers.
Technical Bulletin EOR:83:01:TB (Enorflo-X).
Technical Bulletin from Rhone-Poulenc relating to biopolymer XB-23 (xanthan gum).
Technical Bulletin 10705 from Meyhall Chemical (Jaguar HP-8).
Technical Bulletin 08976 from National Starch (PPE.1042).
Technical Bulletin GC-51 from BF Goodrich (Carbopol Resins).
Technical Bullentin TPD/73 from Allied Colloids Manufacturing Co. (Viscalex HV30).
Technical Bulletin 05530 from Rohn & Haas (Acrysol ASE-60).
Technical Bulletin 09450 from Stapol (Ubatol TR-1138).
Utrachi et al, J. Polymer Sci., 5:853 (1967).
Simha et al, J. Polymer Sci., A, I:1089 (1963).

Primary Examiner—Robert L. Stoll
Assistant Examiner—Daniel S. Metzmaier
Attorney, Agent, or Firm—Ronald A. Koatz

[57] ABSTRACT

A liquid system includes a liquid medium and a thickening mixture, the thickening mixture being dispersed in the liquid medium and comprising a synergistic mixture of a gum-type polymer and an acrylic-type polymer. The thickening system is applicable to a wide variety of systems, including detergent and cleaning compositions.

11 Claims, 4 Drawing Sheets

TYPICAL LOG VISCOSITY VS LOG CONCENTRATION PLOT FOR AN AQUEOUS POLYMER SOLUTION

TYPICAL LOG VISCOSITY VS LOG CONCENTRATION PLOT FOR AN AQUEOUS POLYMER SOLUTION

TYPICAL SIGMOID CURVE FOR A GUM-TYPE POLYMER JAGUAR HP60 AT pH 9-10

VARIATION IN SYNERGY WITH CARBOPOL 910 LEVEL
FOR A 0.1% SHELLFLO XA SOLUTION IN THE PRESENCE/ABSENCE OF NaCl

LEGEND
■ 3% NaCl
□ NO SALT

LOG VISCOSITY VS LOG CONCENTRATION
FOR PPE1042 AT pH 9-10

THICKENING SYSTEM

This is a continuation of Ser. No. 07/713,050, filed Jun. 10, 1991, now abandoned, which is a continuation of U.S. Ser. No. 07/361,514, filed Jun. 5, 1989, now abandoned.

THICKENING SYSTEM

The present invention relates to a synergistic thickening system. More particularly, it relates to a mixture of two different thickening agents which yields a synergistic thickening effect in liquid media.

In very many areas of industry, thickening agents are used to impart a certain rheological behaviour to liquid media. By thickening such liquid media, they can be made more suitable for their end-use, or they can be made more suitable as an intermediate medium in which other substances can be included which need to remain stable suspended or dispersed in the media. By varying the levels of thickening agents, the degree of thickening can be controlled.

A vast number of thickening agents is known in the art, and many of them have found practical application. Since frequently, however, the thickening agent does not contribute anything more than a thickening effect, one attempts to use as little as possible of the thickening agent, since these thickening agents may be rather expensive. In addition, frequently such thickening agents may be adversely affected by other substances present in the liquid media, e.g. electrolyte salts, which imposes restrictions on their use for particular purposes.

Of the known thickening agents, the class of the organic, polymeric thickening agents is perhaps the best known. Among these organic, polymeric thickening agents, the gums feature as a class of widely used thickening agents. Gums or mucilages basically consist of polysaccharides with varying polymerization degrees.

They include the polysaccharide hydrocolloids, which are usually prepared from gums, and they may have been chemically modified, e.g. by partial acetylation, to make them more water-soluble and/or stable in the presence of the other ingredients in the liquid media. Biopolymers also belonging to this class of polysaccharide hydrocolloids are known thickening agents. Typical examples of commercially available, gum-type thickening agents are xanthan gums and their derivatives. These include a partially acetylated xanthan gum, KELZAN ex Kelco Company of N.J., USA, SHELLFLO-XA and ENORFLO-XA, xanthan gums ex Shell Chemicals Ltd., and Rhodapol, a xanthan gum ex Rhone-Poulenc SA. A further example is the biopolymer Shellflo S, a succinoglucan ex Shell Chemicals Ltd. Yet other gum-type thickening agents are those derived from guar gums, such as the JAGUAR(R) products ex Stein, Hall and Co Inc. and those derived from cellulose such as carboxymethyl or hydroxyethyl cellulose.

The present invention is particularly concerned with the above gum-type thickening agents.

Another group of well-known, organic thickening agents are the synthetic, polymers which include acrylate homo- or coplymers and derivatives thereof. Typical examples of such materials which are suitably cross-linked are the acrylic copolymers sold by National Starch and Chemical Ltd under the trade names EP 1910 and PPE 1042. Other types of such (meth)acrylic homo- and copolymers are certain Carbopol(R)-type, cross-linked carboxyvinyl polymers such as CARBOPOL(R)-940 ex B. F. Goodrich Co Ltd. Other examples are the Viscalex products ex Allied Colloids, which are emulsions of (meth)acrylic acid copolymers with (meth) acrylate esters, e.g. VISCALEX HV 30, ACRYSOLS (ex Rohm & Haas) and UBATOLS (ex Stapol).

The present invention is particularly concerned with the synthetic acrylate copolymer-type thickening agents.

Both the gum-type and the acrylic copolymer-type thickening agents that, in general, the viscosity ($\eta$) of a Patent Application 0 174 689, published on Mar. 19, 1986. in which representatives of both types have been described for inclusion in shear-thinning liquid cleaning compositions. This publication is hereby incorporated by way of Reference.

It is well known in the field of organic, polymeric thickening agents that, in general, the viscosity ($\tau$) of a liquid is dependent on the concentration of thickening agent in that liquid. This relationship can be expressed schematically as a sigmoid curve as shown in FIG. 1 which is a plot of log $\eta$ vs log c for the thickening agent in the given liquid. While not wishing to be bound by any theory, we believe that in region A the molecules are essentially independent of one another, the viscosity increase arises from disruption of flow of the continuous phase, and the rate of increase is relatively small. In region B the molecules are sufficiently close together to interact, entangle etc., and the viscosity rises very steeply. In region C the units are close packed and increasingly experience compression so that once again the rate of increase in viscosity is relatively small.

Region A is defined as that portion of the sigmoid curve where the viscosity of the total system corresponds approximately to that of the base system and there is a linear relationship between log $\eta$ and log c.

Region B (lower) is defined as that portion of the sigmoid curve which obeys a power law relationship (the coefficient of which is greater than 1) beneath the point of inflexion.

Region B (upper) is defined as that portion of the sigmoid curve which obeys a power law relationship (the coefficient of which is greater than 1) above the point of inflexion.

Region C is defined as that portion of the sigmoid curve where the viscosity of the total system is Greater than that of the base system and there is an essentially linear relationship between log $\eta$ and log c.

The point of inflexion for the sigmoid curve is defined as that point where the first derivative of the curve experiences a turning point.

For a given liquid system the position of the sigmoid curve on the log $\eta$ vs log c graph will depend on, for example, polymer type or temperature. It is therefore convenient to describe a given system in terms of a single master curve which represents the actual measured parameter plus a shift factor which superposes the measured curve on the reference curve.

Reference sigmoid curves can be constructed according to the method described in R Simha and L Utracki, J Polymer Sci, A-2, 5, 853 (1967), L Utracki and R Simha, J Polymer Sci, A, I, 1089 (1963) and R Simha and L Utracki, Rheol. Acta, 12,455 (1973), for a liquid system comprising a gum-type polymer and for a liquid system comprising an acrylic-type polymer. Typical sigmoid curves for these systems are shown in FIGS. 2 and 3, which are respectively plots of log $\eta$ vs log c for Jaguar HP60, which is a cellulose derived polymer, and PPE1042 which is a cross-linked acrylic polymer.

According to the present invention there is provided a liquid system including a liquid medium and a thickening mixture, the thickening mixture being dispersed in the liquid medium and comprising a gum type polymer and an acrylic-type polymer, wherein each of the said polymers is selected according to its respective sigmoid curve of log (viscosity) vs log (concentration) for the said liquid medium, each polymer being selected from its sigmoid curve's lower portion having an increasing or substantially constant gradient, the liquid system having a viscosity of at least 20 cPs at a shear rate of 10 sec$^{-1}$ greater than that of the liquid medium in the absence of the said thickening mixture.

It has been found that in liquid compositions so formulated a synergistic thickening effect can be achieved. We have found that many embodiments of the liquid systems according to the invention show synergistic thickening together with shear-thinning, thus providing good flow properties. It is to be understood however that the liquid system of the present invention also extends to pastes thickened by the present thickening mixture.

The synergistic thickening mixture of the present invention can contain more than one of each of the two types of thickening agent.

Figure 1:
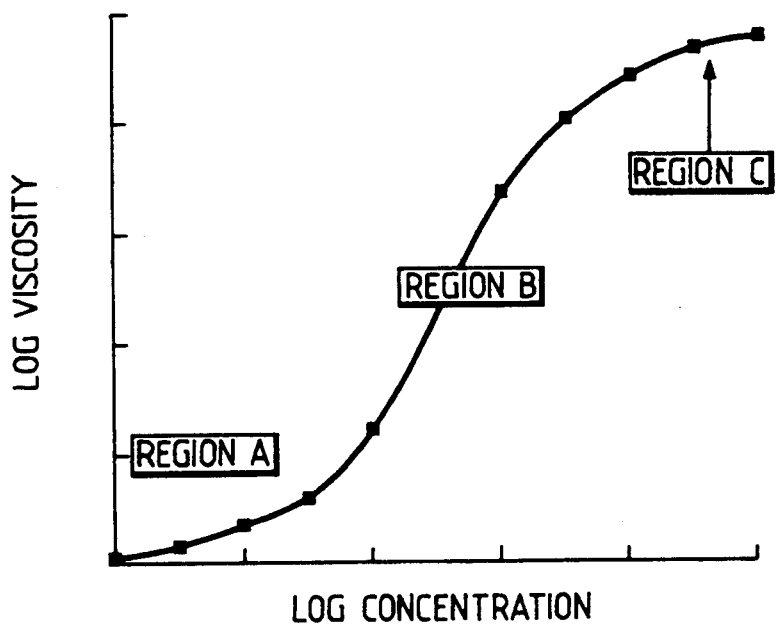
FIG. 1 is a graph of log viscosity plotted against log concentration for a typical aqueous polymer solution.
Figure 2:
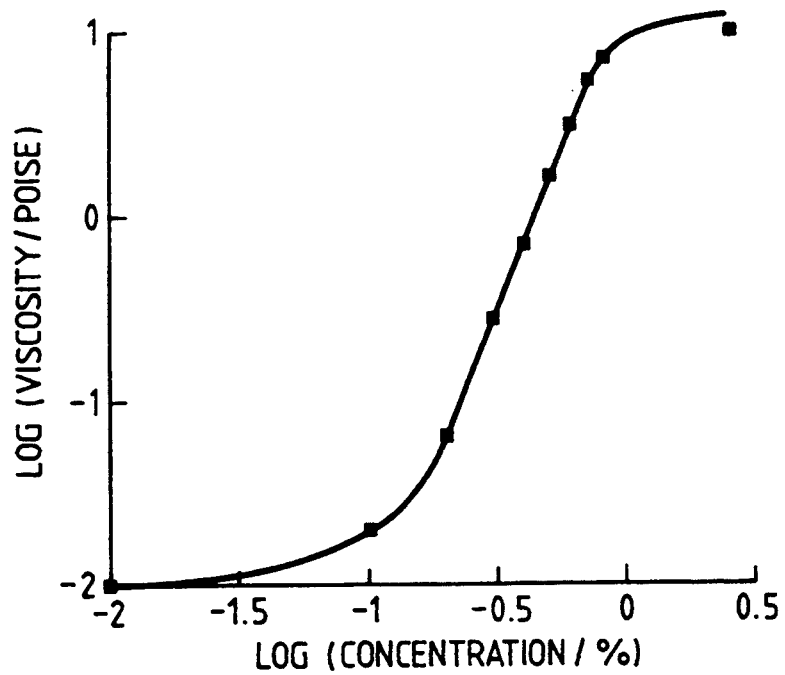
FIGS. 2–6 and FIG. 8 are graphs of log viscosity against log concentration for aqueous solutions of various stated polymers.
Figure 3:
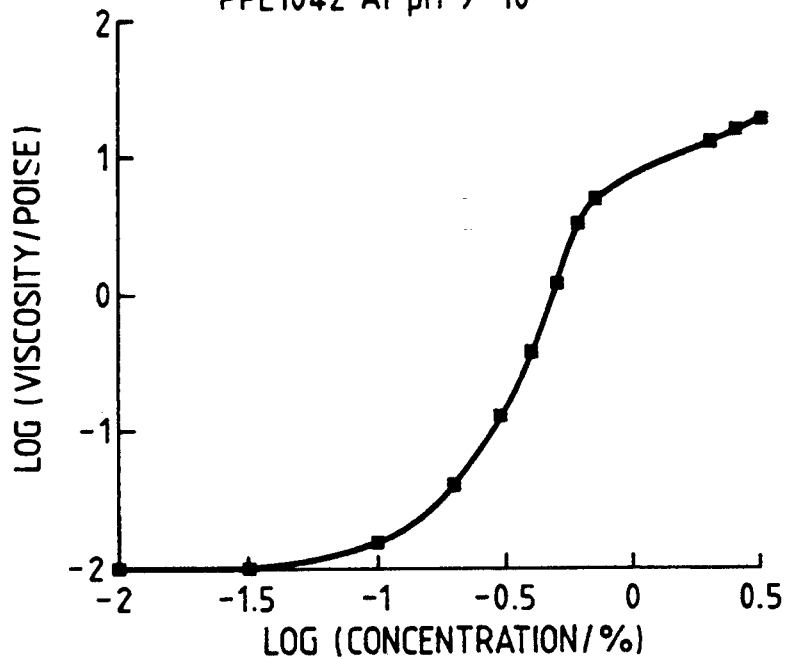

In the ideal case the sigmoid curves for each polymer will be as shown in FIG. 1. The lower portion of the curve from which the present polymers must be selected thus corresponds in the ideal case to region A and region B (lower), subject to the limitation that sufficient polymers must be present to effect an increase in the system of at least 20 cPs at a shear rate of 10 sec$^{-1}$. In practice when the present curves are constructed for a variety of polymers not all polymers follow an ideal sigmoid curve. An overall sigmoid shape can be discerned allowing the presently defined lower portion to be identified i.e. that portion having a constant or increasing gradient and extending between a point near the origin along the curve until the gradient begins to decrease. In some instances however region C may in effect be non-existent as the viscosity at such concentrations may be too high to measure readily or alternatively region C may include a second point of lnflexion. In the latter instance it is only the lower portion of the curve up until the first point of inflexion from which the polymer should be selected. Another non-ideal variant in the shape of the sigmoid curve may include a region of substantially constant gradient between region B (lower) and region B (upper). Such region would fall within the present definition of the lower portion of the curve from which the present polymers must be selected.

It should be noted moreover that the sigmoid curves to be employed are those measured according to the liquid medium in question, ie the log vicosity vs. log concentration plot of each polymer is that of the polymer in the presence of any other ingredients which might be present in the liquid medium.

Preferably the relative weight ratio between the gum-type and the acrylic copolymer-type thickening agent in the thickening mixture ranges from 50:1 to 1:100, preferably from 20:1 to 1:25 and more preferably from 5:1 to 1:10. The amount of thickening agent used for thickening liquid media preferably ranges between 0.01 and 10 wt %, more preferably from 0.1 to 10% by weight of the final product, usually from 0.25 to 5% by weight, and preferably from 0.5 to 1.5% by weight of the final product.

Examples of mixtures of thickening agents embodying the present invention are mixtures of Shellflo-XA with PPF 1042, Shellflo-XA with Carbopol 940, and Shellflo-XA with Viscalex HV30 in appropriate liquid systems.

Figure 4:
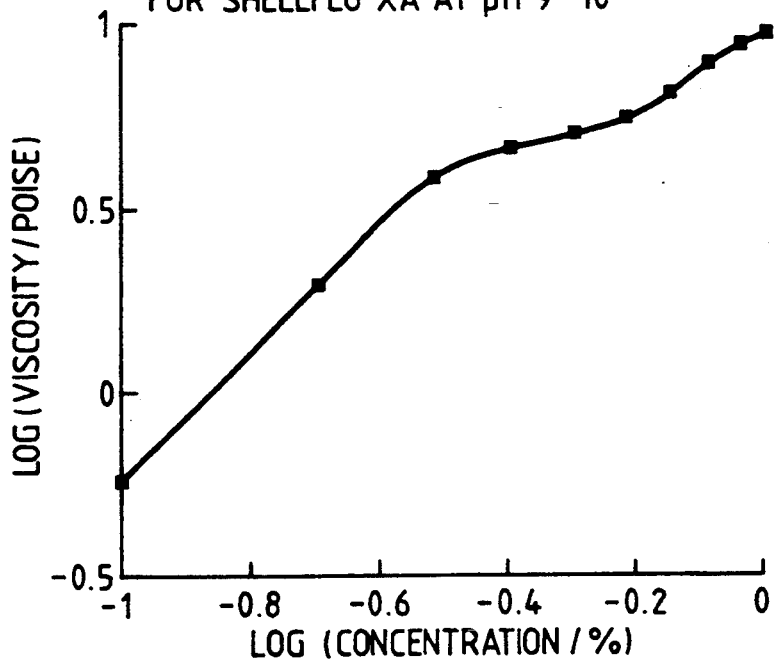
Figure 5:
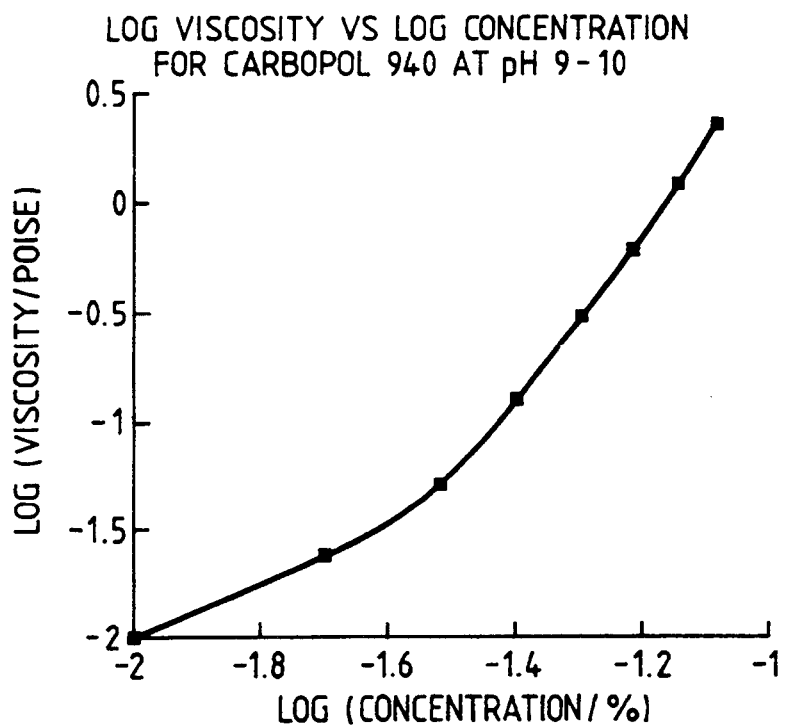
Figure 6:
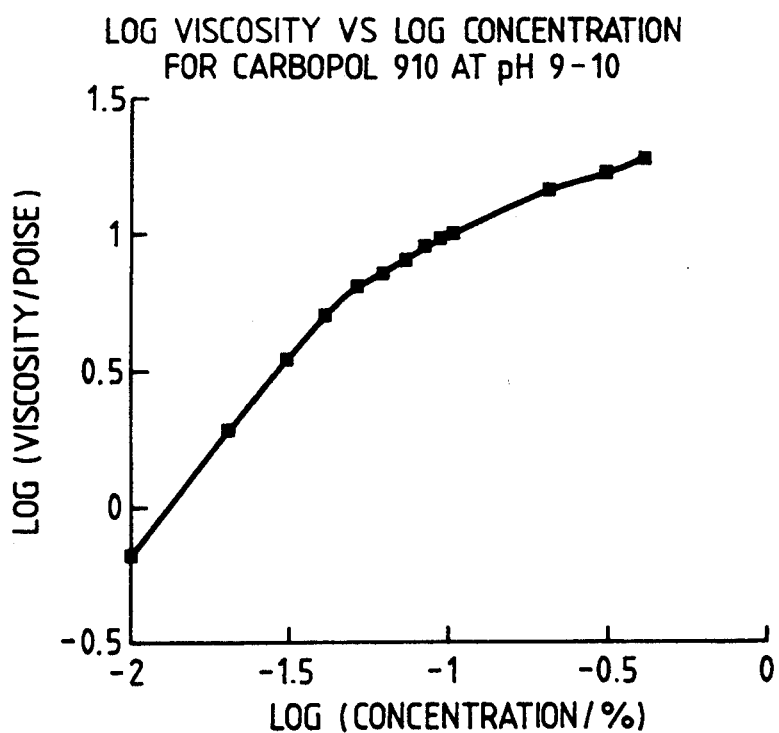
Figure 7:
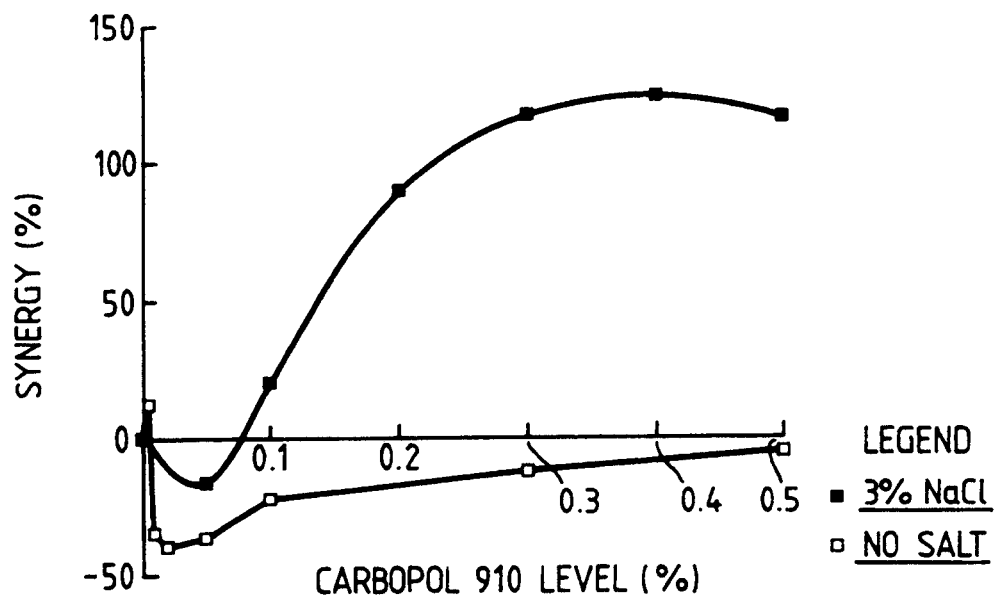
FIG. 7 is a graph showing percentage synergy for Carbopol 910 and Shellflo XA, both in the presence and absence of sodium chloride.

The invention has the added advantage that by altering the variables of a given system it is possible to manipulate otherwise unsuitable polymers into the A region or B (lower) region of their sigmoid curve and obtain the synergistic benefit. For example a mixture of 0.1% Shellflo XA (FIG. 4) with 0.04% Carbopol 940 (FIG. 5) in aqueous dispersion at pH 9.5 gives a synergistic increment of approximately 140% at 25° C., FIGS. 4 and 5 being respectively log $\eta$ vs log c plots in aqueous media at pH 9 to 10 for Shellflo XA and Carbopol 940. Alternatively a mixture of 0.1% Shellflo XA with 0.2% Carbopol 910 in aqueous dispersion at pH 9.5 gives a synergistic increment of approximately −30%. The Carbopol 940 therefore gives the synergistic benefit when mixed with Shellflo XA while Carbopol 910 does not for this particular system. It is believed that the explanation for this difference in behaviour lies in the observation that at 0.2% concentration Carbopol 910 is in the C region of its sigmoid curve for this system. FIG. 6 is a plot of log $\eta$ vs log c for Carbopol 910 in aqueous medium at pH 9 to 10. It follows that if A or B (lower) region behaviour could be induced in the Carbopol 910 by changing the system then the synergistic benefit would be obtained. The addition of 3% salt to a 0.1% Shellflo XA/0.2% Carbopol 910 mixture achieves this and a synergistic increment of 95% is seen. These results are given in FIG. 7 which are plots of synergy in % vs concentration of Carbopol 910 in % for a 0.1% Shellflo XA solution with and without 3% NaCl.

Thus the present liquid systems can include a liquid medium which includes an electrolyte. A preferred level of electrolyte is 0.1 to 10 wt % electrolyte with respect to the liquid medium.

For a particular system the synergistic increment can be calculated according to the equation given below $$S = \left[ \frac{\eta(P_1 + P_2)}{\eta P_1 + \eta P_2} - 1 \right] \times 100$$

where S=the synergistic increment $\eta$ (P$_1$+P$_2$)=the viscosity of a mixture of polymers P$_1$ and P$_2$ $\eta P_1$ = the viscosity of polymer P$_1$ $\eta P_2$ = the viscosity of polymer P$_2$ Preferably the thickening mixture imparts a synergistic increment S of at least 5%, more preferably a synergistic increment of at least 10%, even more preferably a synergistic increment of at least 50%.

The synergistic mixture of the thickening agents according to the present invention can be used for a variety of liquid systems to be thickened. If desired the liquid medium can contain a dispersed phase which could be for example a suspended particulate ingredient, another liquid or a gas.

Examples of the present liquid systems include liquid detergent and cleaning compositions. Suitably such liquid systems contain 0.05 to 20 wt %, more suitably 0.1 to 15 wt %, even more suitably 2 to 10 wt % of a detergent active material selected from the group comprising anionic, nonionic, zwitterionic, cationic detergents and appropriate mixtures thereof. Particularly suitable detergent active materials include soap and synthetic materials such as alkylbenzenesulphonates, alkanesulphonates, alkylsulphates, alkylethersulphates and mixtures thereof, all of which would be compatible for use with an anionic acrylic type polymer. If desired the liquid detergent and cleaning compositions can contain stably suspended particulate detergent ingredients and/or particulate abrasive materials. Other ingredients commonly encountered in such compositions may also be included, such as builders including polymeric builders, sequestering agents, dyes, preservatives, perfumes, bleaches, bleach activators, solvents, enzymes, foam controlling agents and hydrotropes. The liquid medium of the composition is usually an aqueous medium.

Particularly in the field of aqueous, liquid abrasive cleaning compositions, which generally contain from 1% up to 70% of particulate abrasive material, the mixture according to the present invention is of surprising benefit. Such compositions, when containing the present synergistic thickening mixture, can show excellent physical stability as well as improved cleaning and reduced damage, particularly on soft substrates, and can show an improved rinsability when compared with current liquid abrasive cleaners.

It has moreover been found that liquid abrasive cleaners embodying the present invention and containing 30 to 40 wt %, preferably 35 wt %, abrasive particulate material can have the same viscosity as conventionally formulated liquid abrasive cleaners containing about 50 wt % particulate abrasive material. Use of the present thickening system in liquid abrasive cleaners can thus permit more flexibility in formulation. A preferred thickening system for use in liquid abrasive cleaners comprises, with respect to the final liquid system, 0.05 to 1.0 wt % synthetic cross-linked acrylate polymer and 0.05 to 0.7 wt % xanthan gum derivative or mixtures thereof. Suitably a liquid abrasive cleaner contains 0.1 to 10 wt % nonionic surfactant. It is to be understood that the present invention extends to a liquid abrasive cleaner containing 1 to 70 wt % particulate abrasive material and 0.5 to 1.5 wt % thickening mixture, the thickening mixture preferably comprising with respect to the final composition 0.05 to 1.0 wt % synthetic cross-linked acrylate polymer and 0.05 to 0.5 wt % xanthan gum and/or xanthan gum derivative, the cleaner optionally containing 0.1 to 10 wt % nonionic detergent.

Similarly, the synergistic mixture can be used in liquid fabric washing compositions to impart improved suspending properties thereto. A specific area for application is in the field of lavatory cleaners. It has been found that such mixtures according to the invention may have improved shear-thinning and drainage behaviour when compared with mixtures containing acrylate polymers alone. It is to be understood that the present invention extends to a cleaning composition containing 0.02 preferably 0.05 or 0.01 up to 15 or 20 wt % detergent selected form cationic, anionic, nonionic, zwitterionic surfactants and mixtures thereof and 0.5 to 1.5 wt % thickening mixture, the thickening mixture preferably comprising 0.05 to 0.5 wt % synthetic cross-linked acrylate polymers and 0.05 to 1.0 wt % xanthan gum and/or xanthan gum derivative.

Another area of use of the synergistic mixture is the area of personal products such as shampoos, shower and bath gels, lotions, creams, and products for dental care. In this respect, it has surprisingly been found that the inclusion of the synergistic mixture in toothpastes can provide toothpastes which have a higher gloss, a cleaner ribbon break and a smoother texture than toothpastes which have been thickened with the aid of current thickeners, e.g. sodium carboxymethyl cellulose. The present invention thus beneficially extends to a liquid system in the form of toothpaste containing 0.25 to 5 wt % of thickening mixture comprising preferably, with respect to the final composition, 0.2 to 3 wt % synthetic cross-linked acrylate polymer 0.05 to 2 wt % xanthan gum and/or xanthan gum derivative.

A specific area for application is in the field of paper coating where the synergistic mixture can be used as an anti-migrant. Another area for application is in the field of paint formulation where the synergistic mixture can be used as a suspending agent and stabiliser.

Further areas where the synergistic mixture can be used with advantage are the paint and adhesive areas, wallpaper treatment gels and glues, the oil recovery area the oil well drilling area, the suspension polymerization area and so on.

Specific further application areas are:

Abrasives

Rapid grinding action and fast removal of cuttings can be provided, along with excellent suspension of abrasives.

Adhesives

Adhesives will pump readily and have low viscosity, yet have high viscosity under low-shear conditions. Water release during drying can be fast.

Agricultural

The synergistic mixture can be used as a suspending agent for herbicides, pesticides, fertilizers, and fungicides. Owing to its excellent control of drift and cling during spraying, longer contact time can be possible. It can behave as an excellent stabilizer for flowable agrochemicals.

Ceramics

The synergistic mixture can suspend ingredients in glaze and maintain viscosity. Extrusions can be lubricated and green strength can be improved.

Cleaners

The synergistic mixture can promote cling to vertical surfaces for longer contact time and can make possible formulation of gel-type acid and alkali cleaners for industrial applications.

Gels

The synergistic mixture can act as a gelling agent.

Mining

The synergistic mixture can control settling rate of ores during sedimentation, can act as a flocculant in separation processes, and can provide foam stabilization. In slurry pumping, it can give drag reduction and can also suspend, especially under low-shear conditions. It can also be used for shot-firing chemicals.

Paper

The synergistic mixture can be used as an anti-migrant in the paper industry, as a rheology modifier for high solids size press and roll casings, wet-end formation aid, suspension of raw starch for jet cookers, and dewatering control or air knife coatings. It can also be used for rheology control in printing pastes, clay coatings and colour coatings.

Pigments

The synergistic mixture can provide suspension of slurried pigments during shipment and storage and can held control re-agglomeration.

Polish

The synergistic mixture can provide solids suspension in shoe polish, abrasive suspension in silver and brass polish, and emulsion stabilization in wax polish.

Textile

As a suspending agent for dye pigments, the synergistic mixture can control application in space printing and Kuester dyeing and acts as flow modifier during printing application. It can also be used for rheology control in printing pastes.

Wallpaper

The synergistic mixture can be used as a flow modifier and suspending agent during printing. It can also be used for wallpaper- and poster-type adhesives.

Welding Rods

The synergistic mixture can lubricate during extension and can provide green strength.

Deodorant gels

Deodorant gels made with the synergistic mixture can be thermally reversible (when filled hot, they gel upon cooling). Firm, rubbery gels can be produced, which slowly release deodorants.

Fire fighting

Owing to its high viscosity at low concentrations, the synergistic mixture can improve the drop pattern and the cling of the fire-fighting fluid to trees and shrubs.

Paper sizing

Use of the synergistic mixture by the paper industry can enhance the efficiency of rosin-alum sizes, increases Mullen reading, and can improve internal water resistance.

Suspensions

The high yield stress value of the synergistic mixture solutions can provide stable suspensions of a variety of materials.

Various photographic processing

The synergistic mixture can be highly compatible with photo-processing solutions and can be thermally reversible within the temperature range of photo-processing. Smooth surfaces with low syneresis will result.

Soil erosion

The synergistic mixture can be employed successfully in preventing soil erosion.

The synergistic mixture can also be used in other industrial applications such as:

Ink

The synergistic mixture can be used as a suspending agent and stabiliser for water-based and emulsion inks and can provide controlled penetration and water release under uniform gloss.

In suspending applications

For example, shampoos for suspension or anti-dandruff agents.

In stabilisation of emulsions

For example, hand creams, foams, wax polishes, cosmetics, such as lipstick.

In gel-type "cling" applications

For example, acid/neutral cleaners, de-rusting and iron-stain removal in baths, denture fixatives.

The synergistic mixture can be added to the liquid media to be thickened in several ways, but care should be taken to avoid excessive aeration. We have found that a preferred way of incorporating the synergistic mixture in e.g. a liquid abrasive cleaning composition comprises the steps of adding the particulate abrasive material to a dispersion of the gum-type thickening agent at alkaline pH, and subsequently adding the acrylic copoymer-type thickening agent in pre-neutralized form to the resulting dispersion and thereafter adding the remaining ingredients of the composition.

The invention will further be illustrated by way of Example.

EXAMPLE I

The viscosity of various thickening mixtures and individual components of these mixture was measured under the following conditions:

| Shear rate: | $10 \sec^{-1}$ and $110 \sec^{-1}$ |
| --- | --- |
| Temperature: | 25° C. |
| Water: | distilled water |
| Viscosity: | viscosity in mPaS as measured on a Haake RV2 viscometer |

Figure 8:
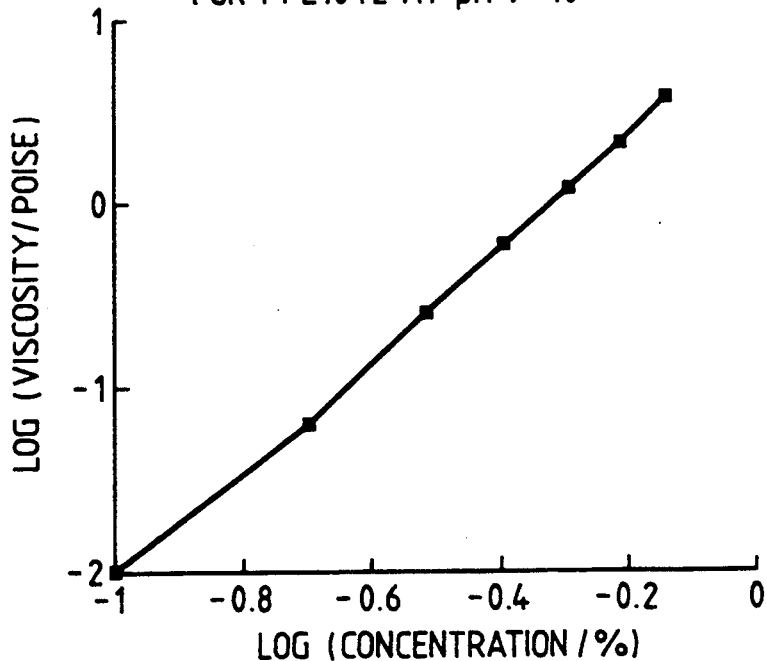

The thickening agents used were Shellflo-XA (FIG. 4) and PPE 1042 (FIG. 8) at a pH of 10.

The following results were obtained:

| | | Viscosity in mPaS | |
| --- | --- | --- | --- |
| % Shellflo-XA | % PPE 1042 | at $10 \sec^{-1}$ | at $110 \sec^{-1}$ |
| 0 | 0 | 1 | 1 |
| 0.01 | 0 | 9.8 | 4.4 |
| 0.1 | 0 | 86.2 | 20 |
| 0.2 | 0 | 206 | 38.4 |
| 0 | 0.5 | 24 | 15.4 |
| 0 | 0.7 | 74.9 | 36 |
| 0 | 0.9 | 180 | 84.7 |
| 0.01 | 0.5 | 52 | 26 |
| 0.1 | 0.5 | 250 | 68.7 |
| 0.2 | 0.5 | 420 | 100.4 |
| 0.01 | 0.7 | 115 | 46.7 |
| 0.1 | 0.7 | 298 | 92.3 |
| 0.2 | 0.7 | 610 | 155.6 |
| 0.01 | 0.9 | 200 | 76.9 |
| 0.1 | 0.9 | 500 | 146.2 |
| 0.2 | 0.9 | 800 | 207.4 |

EXAMPLE 2

Mixtures of 0.1% Shellflo-XA with varying amounts of Carbopol 940 at neutral pH were tested according to Example 1 at a shear rate of $10 \sec^{-1}$. The following results were obtained:

| % Carbopol 940 | % increase in viscosity |
| --- | --- |
| 0 | 0 |
| 0.01 | 20 |
| 0.02 | 65 |
| 0.03 | 110 |
| 0.04 | 140 |
| 0.05 | 140 |
| 0.06 | 80 |
| 0.07 | 35 |
| 0.08 | 10 |

EXAMPLE 3

Repeating Example 2, but using varying amounts of Viscalex HV 30 at neutral pH instead of Carbopol 940, gave the following results:

| % Viscalex HV 30 | % increase in viscosity |
| --- | --- |
| 0 | 0 |
| 0.1 | 15 |
| 0.2 | 65 |
| 0.3 | 75 |
| 0.4 | 35 |
| 0.5 | 5 |

EXAMPLE 4

The following liquid abrasive cleaners were prepared:

| | % by weight | | |
| --- | --- | --- | --- |
| | A | B | C |
| PPE 1042 | 0.1 | 0.5 | 0.9 |
| Shellflo-XA | 0.2 | 0.2 | 0.2 |
| Topped $C_9$-$C_{11}$ linear alcohol condensed with 5 moles of ethylene oxide | 1.5 | 1.5 | 1.5 |
| Perfume | 0.7 | 0.7 | 0.7 |
| Particulate calcite | 50 | 50 | 50 |
| Water | q.s. | q.s. | q.s. |

Glossy, black, ceramic tiles were cleaned with these products and, after rinsing and drying, they were visually assessed as to formation of streaks thereon. As control, a commercially available, liquid abrasive cleaner was used. The following results were obtained:

| | Applied in water of 40° FH at 45° C. | Applied in demineralized water | Used neat |
| --- | --- | --- | --- |
| A | No streaks | No streaks | No streaks |
| B | " | " | " |
| C | " | " | " |
| Control | Streaky | Slighty streaky | White streaky film |

On storing these products A, B and C for 6 months at ambient temperature, no phase separation was observed. In cleaning tests, these products were twice as effective as the control in removing hydrophobic soil from Perspex substrates, and reduced damage to the Perspex surface by half.

EXAMPLE 5

The following liquid abrasive cleaning composition was prepared by mixing the ingredients in the given order of addition:

| Order of ingredient addition | % Composition |
| --- | --- |
| 1. Demineralized water | to 100 |
| 2. Shellflo-XA (at pH 9.8) | 0.02 |
| 3. Particulate calcite | 35.0 |
| 4. Titanium dioxide | 0.5 |
| 5. PPE 1042 (at pH 9.8) | 0.5 |
| 6. Topped $C_9$-$C_{11}$ linear alcohol condensed with 5 moles of ethylene oxide | 1.5 |
| 7. Preservative | 0.05 |
| 8. Perfume | 0.2 |

The viscosity of this product, when made, was 1140 mPAS, and after two weeks' storage at room temperature and at 37° C., the viscosity was 1086 and 942 mPAS, respectively. The pH of the product, when made, was 9.84.

EXAMPLE 6

The following toothpastes were prepared:

| | % by weight | |
| --- | --- | --- |
| Silica (Gasil 200) | 12 | — |
| Alumina (AF 240) | — | 50 |
| Sorbitol | 45 | 27 |
| Sodium lauryl sulphate | 1.7 | 1.7 |
| Sodium dodecyl benzene sulphonate | 0.5 | 0.5 |
| Sodium monofluorophosphate | 0.76 | 0.76 |
| Saccharin | 0.2 | 0.2 |
| Tiona G | 1 | 1 |
| Flavour | 1 | 1 |
| PPE 1042 | 1.8 | 0.7 |
| Shellflo-XA | 0.2 | 0.1 |
| Viscosity in PaS at shear rate (at room temperature, 0.1 sec | 400 | 900 |
| after 5 weeks) 10 sec | 60 | 70 |

These toothpastes were glossier and smoother than a commercially available toothpaste thickened with a Carbopol/sodium carboxymethyl cellulose mixture.

EXAMPLE 7

The following lavatory cleaners were prepared:

| | A | B | C | D | E |
| --- | --- | --- | --- | --- | --- |
| PPE 1042 | | | | | 4.55 |
| Shellflo-XA | 0.2 | 0.2 | 0.25 | 0.25 | — |
| Carbopol 940 | 0.11 | 0.14 | 0.14 | 0.17 | — |
| anionic active[1] | 0.25 | | | | |
| anionic active[2] | 0.25 | | | | |
| nonionic active[3] | 1.5 | | All levels | | |
| Formalin | 0.75 | | unchanged | | |
| Yellow dye | 0.006 | | | | |
| Blue dye | 0.005 | | | | |
| Perfume | 0.7 | | | | |
| Borax | 0.1 | | | | |
| Water | to 100% | | | | |
| Synergy % | 182 | 259 | 252 | 206 | — |
| Residual Mass % after 40 mins. | 20 | 28 | 32 | 35 | 28 |

[1]is alkyl benzene sulphonate
[2]is lauryl ether sulphonate
[3]is alkylethoxylate of $C_9$-$C_{11}$ chain length substituted with 8EO per molecule.

EXAMPLE 8

The following paper coating formulation was prepared:

| | Dry parts by weight |
| --- | --- |
| SPS China Clay | 100 |
| Narlex LD31[1] | 0.3 |
| Sodium hydroxide | 0.15 |
| Emulsion binder[2] | 12.0 |
| Final pH | 9–9.5 |

-continued

| | Dry parts by weight |
|---|---|
| Final solids | 50% |

[1] Narlex LD31 is a low molecular weight sodium polyacrylate polymer
[2] Emulsion binder was vinyl acetate/acylic copolymer To this mixture 0.1% (dry) of SCMC and varying amounts of PPE 1042 were added. Mixtures containing between 0.1 and 0.6% PPE 1042 showed positive synergy. A mixture containing 0.1% SCMC and 0.5% PPE 1042 gave a synergy of 74%.

EXAMPLE 9

The following paint formulation was prepared:

| | Parts by weight |
|---|---|
| Titanium dioxide | 76 |
| Calcium carbonate | 94.4 |
| Narlex LD31[1] | 1.9 |
| Binder emulsion (wet)[2] | 104 |
| Water (as required for 50% s/c) | |
| Pigment vol conc. 50% | |

1 and 2 as in Example 8

To this mixture 0.25% dry weight of Natrosol HHR and varying amounts of PPE 1042 were added. Mixtures containing from 0.1 to 1.6% PPE 1042 (dry weight by weight of paint) showed positive synergy. A mixture containing 0.25% Natrosol HHR and 1.0% PPE 1042 showed a synergy of 75%. Natrosol HHR is a branched hydroxy ethyl cellulose.

EXAMPLE 10

Sea water in a thickened form has applications in the oil field industry. Sea water was used having the following ionic composition:

| | | |
|---|---|---|
| $Na^+$ | 10900 | mg/l |
| $Ca^{2+}$ | 428 | mg/l |
| $Mg^{2+}$ | 1368 | mg/l |
| $K^+$ | 460 | mg/l |
| $Sn^{2+}$ | 8 | mg/l |
| $Cl^-$ | 18700 | mg/l |
| $SO_4^{2-}$ | 2960 | mg/l |
| $HCO_3^-$ | 124 | mg/l |

Experiments performed using a mixture of a xanthan gum (Kelzan XC ex Kelco Company) and a cross-linked polyacrylate (PPE 1087 ex National Starch) to thicken the above sea water composition gave a synergistic increment of 600% when the sea water contained 0.3 wt % xanthan gum (dry) and 1.25 wt % cross-linked polyacrylic polymer. Table 1 lists the synergy S, as defined above, in percentage terms vs concentration of polyacrylic polymer in wt % for a sea water composition containing a constant amount of xanthan gum at 0.3 wt % and clearly shows the synergy in thickening for compositions containing between 0.75 and 1.5 wt %, peaking at 1.25 wt %, cross-linked polyacrylic polymer.

| SYNERGY BETWEEN PPE 1087 AND XANTHAN GUM IN SEA WATER THICKENING | |
|---|---|
| % PPE 1087 (DRY) | % SYNERGY |
| 0.75 | 140 |
| 1.00 | 300 |
| 1.25 | 600 |
| 1.5 | 110 |

I claim:

1. A toothpaste composition comprising:
   (i) a aqueous liquid medium;
   (ii) detergent selected from the group consisting of anionic, nonionic, zwitterionic and cationic detergents and mixtures thereof, in an amount from 0.02 to 20 wt. % based on the liquid medium;
   (iii) particulate solid abrasive in an amount from 1 to 70 wt.% based on the liquid medium, stably suspended in the liquid medium;
   (iv) a thickening mixture of polymers dispersed in the liquid medium in an amount of 0.025 to 5 wt. % based on the total of the liquid medium and thickening mixture, said mixture consisting of a thickening polymer which is a xanthan gum and a thickening polymer which is a cross-linked acrylic-type polymer selected from the group consisting of synthetic cross-linked acrylate homopolymers and copolymers and mixture thereof,
   wherein said gum-type polymer and said acrylic-type polymer are present in a weight ratio of gum-type polymer to acrylic-type polymer of between 20:1 and 1:25,
   and wherein each said polymer, when in said liquid medium in the absence of the other said polymer, has a relationship between concentration/and viscosity, measured at a shear rate of 10 sec$^{-1}$ such that a graph of log (viscosity) against log (concentration) is a sigmoid curve with a lower portion in which, over a range of concentrations, the gradient of the graph of log (viscosity) against log (concentration) is constant or increases with log (concentration),
   and wherein the amount of each of said polymers is such that the concentration thereof in the liquid medium lies within said range over which the gradient of that polymer's said curve of log (viscosity) against log (concentration) is constant or increasing,
   the composition having a viscosity of at least 20 cPs at a shear rate of 10 sec$^{-1}$ greater than that of the liquid medium in the absence of the said thickening mixture, the viscosity of the thickening mixture measured in the liquid medium being greater than the sum of the viscosity of the gum-type polymer measured in the liquid medium and the viscosity of the acrylic-type polymer measured in the liquid medium.

2. A liquid cleaning composition comprising:
   (i) a aqueous liquid medium;
   (ii) a detergent selected from the group consisting of anionic, nonionic, zwitterionic and cationic detergents and mixtures thereof, in an amount from 0.02 to 20 wt. % based on the liquid medium;
   (iii) particulate solid abrasive in an amount from 1 to 70 wt. % based on the liquid medium, stably suspended in the liquid medium;
   (iv) a thickening mixture of polymers dispersed in the liquid medium, in an amount of 0.01 to 5 wt. % based on the total of the liquid medium and thickening mixture, said mixture consisting of 0.05 to 0.5wt. % based on the liquid medium of a thickening polymer which is xanthan gum and a thickening polymer which is a cross-linked acrylic-type polymer selected from the group consisting of synthetic cross-linked acrylate homopolymers and copolymers and mixture thereof, wherein said xanthan gum and said acrylic-type polymer are present in a weight ratio xanthan to acrylic-type polymer of between 20:1 and 1:25;

and wherein each said polymer, when in said liquid medium in the absence of the other said polymer, has a relationship between concentration and viscosity, measured at a shear rate of 10 sec$^{-1}$ such that a graph of log (viscosity) against log (concentration) is a sigmoid curve with a lower portion in which, over a range of concentrations, the gradient of the graph of log (viscosity) against log (concentration) is constant or increases with log (concentration), and wherein the amount of each of said polymers is such that the concentration thereof in the liquid medium lies within said range over which the gradient of that polymer's said curve of log (viscosity) against log (concentration) is constant or increasing, the composition having a viscosity of a least 20 cPs at a shear rate of 10 sec$^{-1}$ greater than that of the liquid medium in the absence of the said thickening mixture.

3. A composition according to claim 2 wherein the thickening mixture is present at a level between 0.25 and 5 wt % with respect to the liquid system.

4. A composition according to claim 2 further comprising electrolyte in an amount of 0.1 to 10 wt % based on the liquid medium.

5. A composition according to claim 2 wherein the viscosity of the thickening mixture measured in the liquid medium exceeds by more than 5% the sum of the viscosity of the gum-type polymer measured in the liquid medium and the viscosity of the acrylic-type polymer measured in the liquid medium.

6. A composition according to claim 2 wherein the amount of detergent is 0.05 to 15 wt % and the amount of the thickening mixture if 0.5 to 1.5 wt %.

7. A composition according to claim 6 wherein the amount of acrylate-type polymer is 0.05 to 1.0 wt % and the amount of xanthan gum is 0.05 to 0.5 wt %.

8. A composition according to claim 2 which is in the form of a toothpaste and wherein the amount of acrylate type polymer is 0.5 to 3 wt % and the amount of xanthan gum is 0.05 to 0.5 wt %.

9. A composition according to claim 2, wherein said solid abrasive comprises calcite.

10. A liquid abrasive cleaning composition comprising;
(i) a aqueous liquid medium;
(ii) detergent selected from the group consisting of anionic, nonionic, zwitterionic and cationic detergents and mixtures thereof, in an amount from 0.05 to 15 wt. % based on the liquid medium;
(iii) particulate solid abrasive in an amount from 1 to 70 wt. % based on the liquid medium, stably suspended in the liquid medium;
(iv) a thickening mixture of polymers dispersed in the liquid medium in an amount of 0.01 to 5 wt. % based on the total of the liquid medium and thickening mixture, said mixture consisting of a thickening polymer which is xanthan gum and a thickening polymer which is a cross-linked acrylic-type polymer selected from the group consisting of synthetic cross-linked acrylate homopolymers and copolymers and mixture thereof, wherein said xanthan gum and said acrylic-type polymer are present in a weight ratio xanthan gum to acrylic-type polymer of between 20:1 and 1:25, and wherein each said polymer, when in said liquid medium in the absence to the other said polymer, has a relationship between concentration and viscosity, measured at a shear rate of 10 sec$^{-1}$ such that a graph of log (viscosity) against log (concentration) is a sigmoid curve with a lower portion in which, over a range of concentrations, the gradient of the graph of log (viscosity) against log (concentration) is constant or increases with log (concentration), and wherein the amount of each of said polymers is such that the concentration thereof in the liquid medium lies within said range over which the gradient of that polymer's said curve of log (viscosity) against log (concentration) is constant or increasing, the composition having a viscosity of at least 20 cPs at a shear rate of 10 sec$^{-1}$ greater than that of the liquid medium in the absence of the said thickening mixture, the viscosity of the thickening mixture measured in the liquid medium being greater than the sum of the viscosity of the xanthan gum measured in the liquid medium and the viscosity of the acrylic-type polymer measured in the liquid medium.

11. A composition according to claim 10, wherein said solid abrasive comprises calcite.

* * * * *